United States Patent [19]
Resnick et al.

[11] Patent Number: 5,978,438
[45] Date of Patent: Nov. 2, 1999

[54] WIDEBAND NON-CONTACT DATA LINK USING X-RAY SOURCES TO EXCITE SCINTILLATING MATERIAL RECEIVING DEVICE

[75] Inventors: Theodore A. Resnick, Beachwood; David A. Wilcox, Chesterland; Rodney A. Mattson, Mentor, all of Ohio

[73] Assignee: Picker International, Inc., Highland Heights, Ohio

[21] Appl. No.: 08/992,866

[22] Filed: Dec. 12, 1997

[51] Int. Cl.$^6$ ...................................................... H05G 1/60
[52] U.S. Cl. ................................................. 378/4; 378/15
[58] Field of Search .................................. 378/4, 15, 19, 378/10, 91, 101, 102; 385/26

[56] References Cited

U.S. PATENT DOCUMENTS

| | | |
|---|---|---|
| 4,739,168 | 4/1988 | Aoki . |
| 4,775,992 | 10/1988 | Resnick et al. . |
| 4,969,167 | 11/1990 | Zupancic et al. . |
| 5,012,505 | 4/1991 | Zupancic et al. . |
| 5,031,198 | 7/1991 | Deucher et al. . |
| 5,081,663 | 1/1992 | Gerlach et al. . |
| 5,220,588 | 6/1993 | Deucher et al. . |
| 5,299,249 | 3/1994 | Burke et al. . |
| 5,475,729 | 12/1995 | Mattson et al. . |
| 5,610,968 | 3/1997 | Deucher et al. . |

OTHER PUBLICATIONS

Literature entitled "Scintillating Optical Fibers" No Date.
Schleifring und Apparatebau GmbH brochure entitled "New Technologies SAF," Release 1.2, Mar. 10, 1997.
Schleifring literature entitled "New Technologies" No Date.

*Primary Examiner*—David P. Porta
*Attorney, Agent, or Firm*—Fay, Sharpe, Fagan, Minnich & McKee, LLP

[57] ABSTRACT

A radiographic scanner (10) has a stationary gantry portion (12) defining a subject receiving region (16) and a rotating gantry portion (20) on which an imaging x-ray tube (22) is mounted. The rotating gantry portion (20) is rotatably mounted to the stationary gantry portion (12) for rotation about the subject receiving region (16). A slip ring assembly extending around the subject receiving region (16) connected with the stationary and rotating gantry portions, includes a scintillating optical fiber (44) mounted around the patient receiving region (16) to one of the rotating and stationary gantry portions. A communication x-ray tube (40) is mounted to the other gantry portion and directed such that radiation therefrom enters the scintillating optical fiber (44) from a lateral direction. The scintillating optical fiber (44) converts the incident x-rays (52) to light (58) and transmits the light (58) along its longitudinal axis. The scintillating optical fiber (44) is enclosed in a protective sheathing (50) that is opaque to optical radiation which protects the fiber from damage and eliminates noise, inaccuracy, and false signals caused by ambient and stray light entering the fiber.

20 Claims, 6 Drawing Sheets

Fig. 6 ined with the transfer of data between moving and stationary gantry portions of CT scanners and will be described with particular reference thereto. However, it is to be appreciated that the present invention also find application in conjunction with data transfer and/or communication in other environments.

WIDEBAND NON-CONTACT DATA LINK USING X-RAY SOURCES TO EXCITE SCINTILLATING MATERIAL RECEIVING DEVICE

BACKGROUND OF THE INVENTION

The present invention relates to the art of non-contact data linking, particularly the communication of data between structures which are moving relative to one another. The invention finds particular application in conjunction with the transfer of data between moving and stationary gantry portions of CT scanners and will be described with particular reference thereto. However, it is to be appreciated that the present invention also find application in conjunction with data transfer and/or communication in other environments.

Typically, a patient is positioned in a supine position on a horizontal couch through a central bore of a stationary gantry of a CT scanner. An imaging x-ray tube is mounted on a rotatable gantry portion and rotated around the patient and central bore. Slip ring assemblies provide data and power communication between the rotating and stationary gantry portions. Arrays of brush assemblies are positioned to make electrical contact with the slip ring in order to provide an electrical path for the transfer of data and communication signals between the stationary and rotating gantries.

Prior art brush assemblies use brushes which are delicate and easily damaged. Often, individual brush assemblies are not replaced and the whole relatively expensive brush block must be replaced. Under rotation opposite the usual direction, the brushes may hang up, buckle, and experience sudden catastrophic failure. In applications such as CT scanners, redundant bulky cartridges are often employed. The use of only one brush per ring tends to cause loss of communication due to skipping. When a brush is biased against the slip ring by a relatively large force to reduce skip, brush life is reduced due to the frictional wear between the brush and slip ring. The increased biasing also tends to cause hang ups or stick. Further, dust and contaminants settle on the exposed slip rings leading to noise, particularly noticeable in high speed communications. This leads to costly maintenance and the need for replacement parts.

More recently, another type of data link has been proposed which has implications for CT scanners. A fluorescent optical rotary joint is a non-contact data link whereby modulated light from an LED is fed laterally into an optical fiber to excite an imbedded fluorescent dye along the length of the fiber. Light which is emitted from the fluorescent dye at relatively flat angles with regard to the longitudinal direction of the fiber is subject to total internal reflection and is launched down the length of the fiber. In one type of prior art data link, the optical fiber is a continuous loop and the LED is rotated relative to the loop. However, this type of data link is accompanied by some inherent drawbacks. Dust, dirt, or other contaminants on the outer surface of the optical fiber interfere with the coupling of light from the LED as it is laterally fed into the optical fiber. This introduces noise into the signal and attenuates the signal, limiting dynamic range. Furthermore, there must be extremely accurate alignment between the LED and fiber. Care must be taken the prevent wobble and to keep the optical path between the LED and fiber optic free of obstruction. The delicate fiber is exposed not only to damage and dirt, but also to external ambient and stray light which can excite the dye and be launched down the fiber creating noise, inaccuracy, and false signals.

The present invention contemplates new and improved non-contact data link assemblies which overcome the above-referenced problems and others.

SUMMARY OF THE INVENTION

In accordance with one aspect of the invention, a radiographic scanner is provided. The scanner includes a stationary gantry portion which defines a subject receiving region. The scanner also has a rotating gantry portion on which a first source of penetrating radiation is mounted. The rotating gantry portion is rotatably mounted to the stationary gantry portion for rotation about the subject receiving region. The scanner also includes a non-contact data link assembly extending around the subject receiving region connected with both the stationary and rotating gantry portions. The non-contact data link assembly includes a light tube including a scintillator mounted to extend around the subject receiving region to one of the rotating and stationary gantry portions. The data link assembly includes a second source of penetrating radiation mounted to the other gantry portion. The second source of penetrating radiation is directed such that radiation therefrom enters the light tube. The scintillator optical fiber converts the incident radiation to light and transmits the light along a longitudinal axis of the light tube.

In accordance with a more limited aspect of the present invention, a radiographic scanner is provided in which the light tube is a scintillating optical fiber enclosed in a protective light opaque sheeting.

In accordance with a more limited aspect of the present invention, the radiographic scanner further includes a circuit for modulating radiation from the second source of penetrating radiation.

In accordance with a more limited aspect of the present invention, the light tube of the radiographic scanner extends along a plane transverse to an axis of rotation of the rotating gantry portion relative to the stationary gantry portion. The scintillating optical fiber forms a loop around the subject receiving region.

In accordance with a more limited aspect of the present invention, the data link assembly and the radiographic scanner communicate control signals, for controlling the first source of penetrating radiation, from the stationary gantry portion to the rotating gantry portion.

In accordance with a more limited aspect of the present invention, the data link assembly of the radiographic scanner communicates monitoring signals, for monitoring operation of the first source of penetrating radiation, from the rotating gantry portion to the stationary gantry portion.

In accordance with another aspect of the present invention, a radiographic scanner is provided. The radiographic scanner includes a stationary gantry portion which defines a subject receiving region and a rotating gantry portion on which a first source of penetrating radiation is mounted. The rotating gantry portion is rotatably mounted to the stationary gantry portion for rotation about the subject receiving region. The scanner also includes a non-contact data link assembly extending around the subject receiving region connected with the stationary and rotating gantry portions. The non-contact data link assembly includes a light tube having reflective surfaces and a scintillating strip disposed therein. The light tube is mounted around the subject receiving region to one of the rotating and stationary gantry portions. The non-contact data link assembly also includes a second source of penetrating radiation mounted to the other gantry portion and directed such that radiation therefrom enters the light tube, the scintillating strip converts incident radiation to light and the light is reflected by the reflective surfaces down a longitudinal access of the light tube.

In accordance with a more limited aspect of the present invention, the light tube is enclosed in a protective light opaque sheath.

In accordance with another aspect of the present invention, a non-contact data link assembly for conveying data between rotary and stationary gantry portions of a CT scanner is provided. The CT scanner includes a stationary gantry portion having a patient receiving region and a rotating gantry portion on which an imaging x-ray tube is mounted for continuous rotation around the patient receiving region about an axis of rotation. The CT scanner includes a slip ring extending around the patient receiving region connected to one of the stationary and rotating gantry portions. A brush assembly connected to the other gantry portion and in sliding contact with the slip ring for at least conveying electrical power to the first x-ray tube is also included. Radiation detectors are mounted to one of the stationary and rotating gantry portions for detecting radiation from the imaging x-ray tube. A reconstruction processor is included for reconstructing an image from the output of the detectors to be displayed on a human viewable display. The non-contact data link assembly comprises a scintillating optical fiber mounted adjacent to the slip ring in a plane orthogonal to the axis of rotation. The scintillating optical fiber has an imbedded radiation sensitive dopant along its length that emits optical light when excited by incident radiation. The non-contact data link assembly also includes a source of non-optical penetrating radiation mounted to the other one of the stationary and rotating gantry portions in the plane of the scintillating optical fiber such that radiation therefrom enters the scintillating optical fiber. The scintillating fiber converts the incident radiation therein to optical light and transmits the light along a longitudinal axis of the fiber.

In accordance with a more limited aspect of the present invention, the non-contact data link assembly includes a scintillating optical fiber that is covered in a protective sheathing opaque to optical radiation.

In accordance with a more limited aspect of the present invention, the non-contact data link assembly includes means for modulating the non-optical penetrating radiation.

In accordance with a more limited aspect of the present invention, the scintillating optical fiber of the non-contact data link assembly forms a complete loop around the patient receiving region.

In accordance with a more limited aspect of the present invention, a signal for controlling the imaging x-ray tube is transferred across the non-contact data link assembly.

In accordance with a more limited aspect of the present invention, a non-contact data link assembly in a CT scanner is provided wherein the radiation detectors are mounted to the rotating gantry portion and the output of the radiation detectors is connected to a modulator which modulates the source of non-optical penetrating radiation. The source of non-optical penetrating radiation is mounted to the rotating gantry portion and generates a signal which corresponds to the output of the radiation detectors. The signal is transferred across the non-contact data link assembly to the scintillating optical fiber mounted to the stationary gantry portion. An output of the scintillating optical fiber is connected to an opto-electrical transducer and the opto-electrical transducer is in turn connected to the reconstruction processor.

In accordance with another aspect of the present invention, a method of transferring data between stationary and rotating gantry portions of a scanner is provided. A beam of non-optical radiation is produced. The beam of radiation is modulated. The modulated beam of radiation is directed to a scintillating optical fiber. The radiation incident on the scintillating optical fiber is converted to light. The light is transmitted along a longitudinal axis of the scintillating optical fiber.

In accordance with a more limited aspect of the present invention, a method of transferring data between stationary and rotating gantry portions of a scanner is provided wherein one of (i) a beam of ultraviolet radiation is produced with an ultraviolet source and (ii) a beam of x-ray radiation is produced from an x-ray tube.

In accordance with a more limited aspect of the present invention, a method of transferring data between stationary and rotating gantry portions of a scanner is provided wherein the modulation of the x-ray beam includes modulating one of a cathode to grid potential and a signal driving a cathode of the x-ray tube to vary an intensity of an electron beam within the x-ray tube.

In accordance with a more limited aspect of the present invention, a method of transferring data between stationary and rotating gantry portions of a scanner is provided wherein the modulation of a beam of x-ray radiation is accomplished by deflecting an electron beam within the x-ray tube such that it selectively impinges two different types of anode material.

In accordance with a more limited aspect of the present invention, a method of transferring data between stationary and rotating gantry portions of a scanner is provided wherein the modulation of a beam of x-ray radiation is accomplished by gating the beam of radiation on and off to communicate digitally.

In accordance with a more limited aspect of the present invention, a method of transferring data between stationary and rotating gantry portions of a scanner is provided wherein the modulation of a beam of x-ray radiation is accomplished using a high frequency transformer to modulate anode-cathode potential.

One advantage of the present invention resides in reduced cost associate with brush maintenance and replacement.

Another advantage is the elimination of frictional wear and frictional contact between the gantries for the data link.

Another advantage of the present invention is that the scintillating optical fiber is protected from potential damage.

Another advantage of the present invention is that alignment between the scintillating optical fiber and the x-ray is not as critical as compared to the optical coupling.

Another advantage of the present invention is that dust, dirt, or like contaminants do not interfere with data communication.

Still further advantages of the present invention will become apparent to those of ordinary skill in the art upon reading and understanding the following and detailed description of the preferred embodiments.

BRIEF DESCRIPTION OF THE DRAWINGS

The invention may take form in various parts and arrangements of parts and in various steps and arrangement of steps. The drawings are only for purposes of illustrating the preferred embodiment and are not to be construed as limiting the invention.

FIGS. 5A and 5B are diagrammatic illustrations of the separate channels housing the scintillating optical fiber, in which

DETAILED DESCRIPTION OF THE PREFERRED EMBODIMENT

Figure 1:
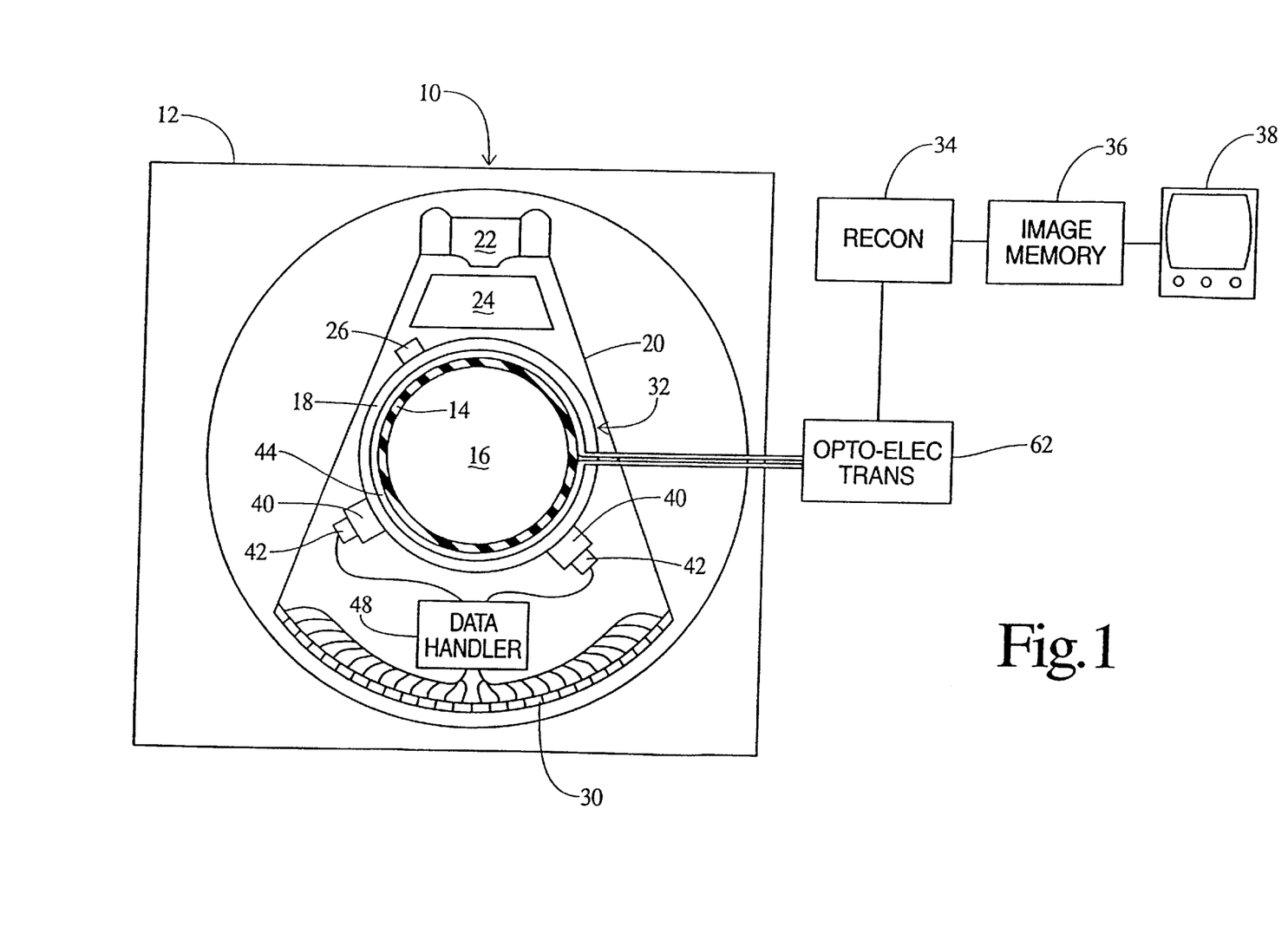
FIG. 1 is a diagrammatic illustration of a scanner in accordance with the present invention, in which radiation detectors are mounted on a rotating gantry portion.

With reference to FIG. 1, a CT scanner 10 includes a stationary gantry portion 12 including a central stationary cylinder 14 that defines a patient or subject receiving region 16. A slip ring assembly 18 is disposed around the stationary cylinder 14.

A rotating gantry portion 20 is mounted on bearings (not shown) to the stationary cylinder 14. The rotating gantry portion 20 includes an imaging x-ray tube 22. A shutter and collimator assembly 24 shapes the emitted radiation into a fan-shaped sheet directed at the central patient receiving region 16 and selectively gates the radiation through the region and blocks it. A power brush assembly 26 rotates along an electromechanical slip ring to transfer power from a power source to the x-ray tube 22. Communication between the stationary and rotating gantry portions is accomplished via a non-contact data link assembly 32 (shown in FIGS. 2A and 2B). Radiation from the imaging x-ray tube 22 which has traversed the subject receiving region 16 defined within the stationary cylinder 14 impinges upon an array of radiation detectors 30. The output from the radiation detectors 30 is reconstructed by an imaging or reconstruction processor 34 which implements a conventional reconstruction algorithm, such as a convolution and back projection algorithm. The image representation is stored in memory 36 for display on a video monitor 38.

Figure 2A:
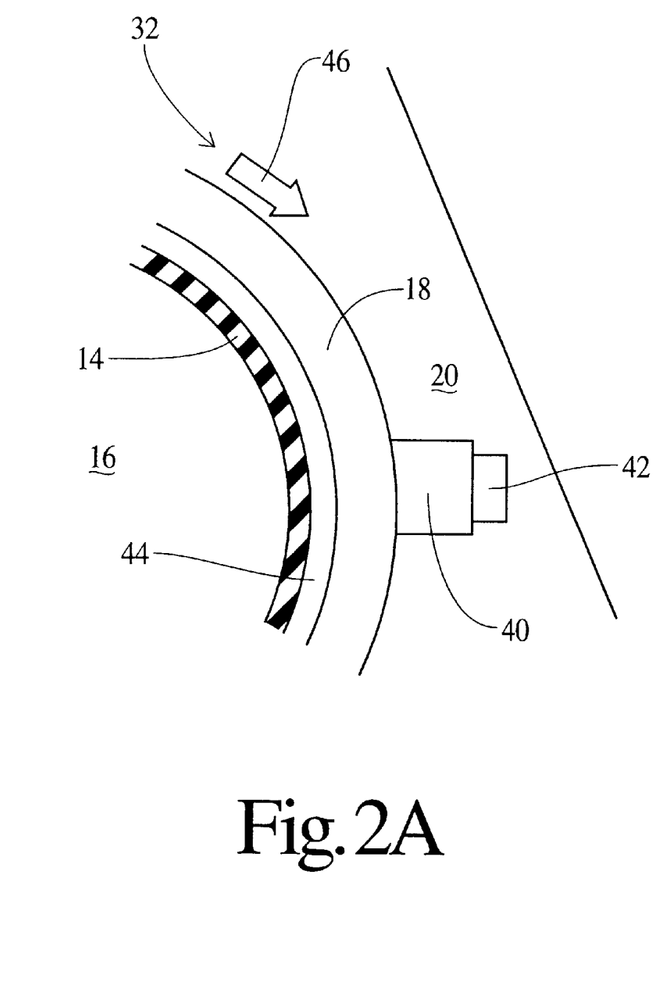
FIGS. 2A and 2B are partial diagrammatic illustrations of a non-contact data link assembly in accordance with an aspect of the present invention, wherein the figures show communication from a rotating to stationary gantry portion and from a stationary to rotating gantry portion respectively.
Figure 2B:
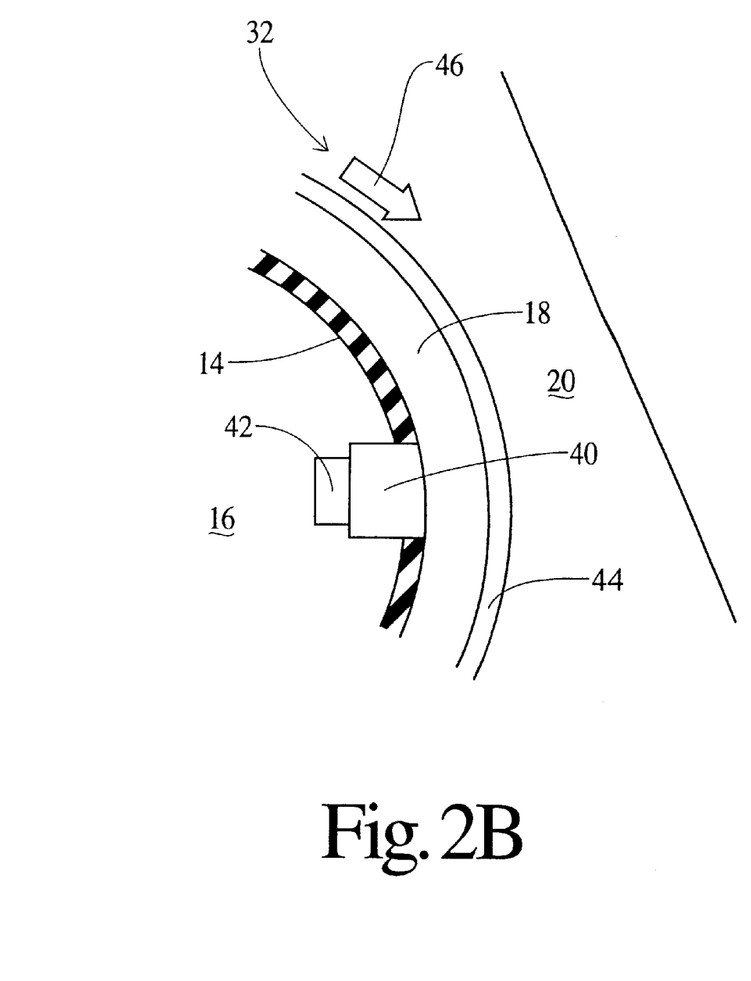

With continuing reference to FIG. 1 and further reference to FIGS. 2A and 2B, the non-contact data link assembly 32 includes a low energy source of non-optical penetrating radiation 40, such as a communication x-ray tube, which is controlled by a modulation and control circuit 42 to modulate the x-ray output in accordance with the information to be communicated. Typical communication signals include control signals for controlling operation of the imaging x-ray tube 22 and the shutter and collimator assembly 24, output signals from elements for monitoring operation of components on the rotating gantry portion 20, and the like. Preferably, the low energy source of non-optical penetrating radiation 40 includes a single or multiple anode and cathode x-ray tube, of relatively small dimensions, able to accommodate the low kV and high band-width of the system. Depending on the system design, modulation is accomplished by modulating the cathode to grid potential to vary the intensity of the electron beam and, correspondingly, the intensity of the x-ray beam produced. Alternately, modulation is accomplished by holding the cup or grid fixed while driving the cathode with a control or modulating signal. This produces a relatively low impedance input and partially decouples the anode to grid voltage changes to help maintain the high band width required. Gating the beam of the radiation on and off to communicate digitally is another method of modulating the x-ray beam. In one embodiment, this is accomplished by moving the beam such that the resultant radiation is available or blocked from exiting the tube. Another modulation method is to deflect the electron beam within the x-ray tube such that it impinges two different types of anode material, thereby drastically changing the amount and quality of the radiation output from the x-ray tube. Another alternative modulation method incorporates a high frequency transformer in the path of the anode or cathode current. This method sums a data signal with the fixed anode to cathode drive potential, and causes modulation of the x-ray intensity as an exponential function of the applied signal. The affect at low kV can be an order of magnitude larger than the applied signal, providing gain in the modulating process and reducing the design difficulty of a high frequency, high voltage system. Establishing voltage swing such that the low voltage resultant radiation is cut off by appropriate filters and higher voltage resultant radiation is allowed to pass in essence creates a digital output in radiation.

Turning now to the non-contact data link assembly 32, for transmission of signals from the rotating to the stationary gantry portion (shown is FIG. 2A), the source of non-optical penetrating radiation 40 is mounted to the rotating gantry portion 20. A scintillating optical fiber 44 for receiving the x-ray signal is mounted to the stationary gantry portion 12 via cylinder 14. Alternately, for transmitting signals from the stationary to the rotating gantry portions (shown in FIG. 2B), the radiation source is mounted to the stationary gantry portion 12 via cylinder 14 and the scintillating optical fiber 44 is mounted to the rotating gantry portion 20. The scintillating optical fiber 44 is positioned adjacent the slip ring assembly 18 mounted to one of the stationary and rotating gantry portion around the subject receiving region 16. Arrow 46 in the drawings indicates the relative rotation of the rotating gantry portion 20 to the stationary gantry portion 12.

Figure 3:
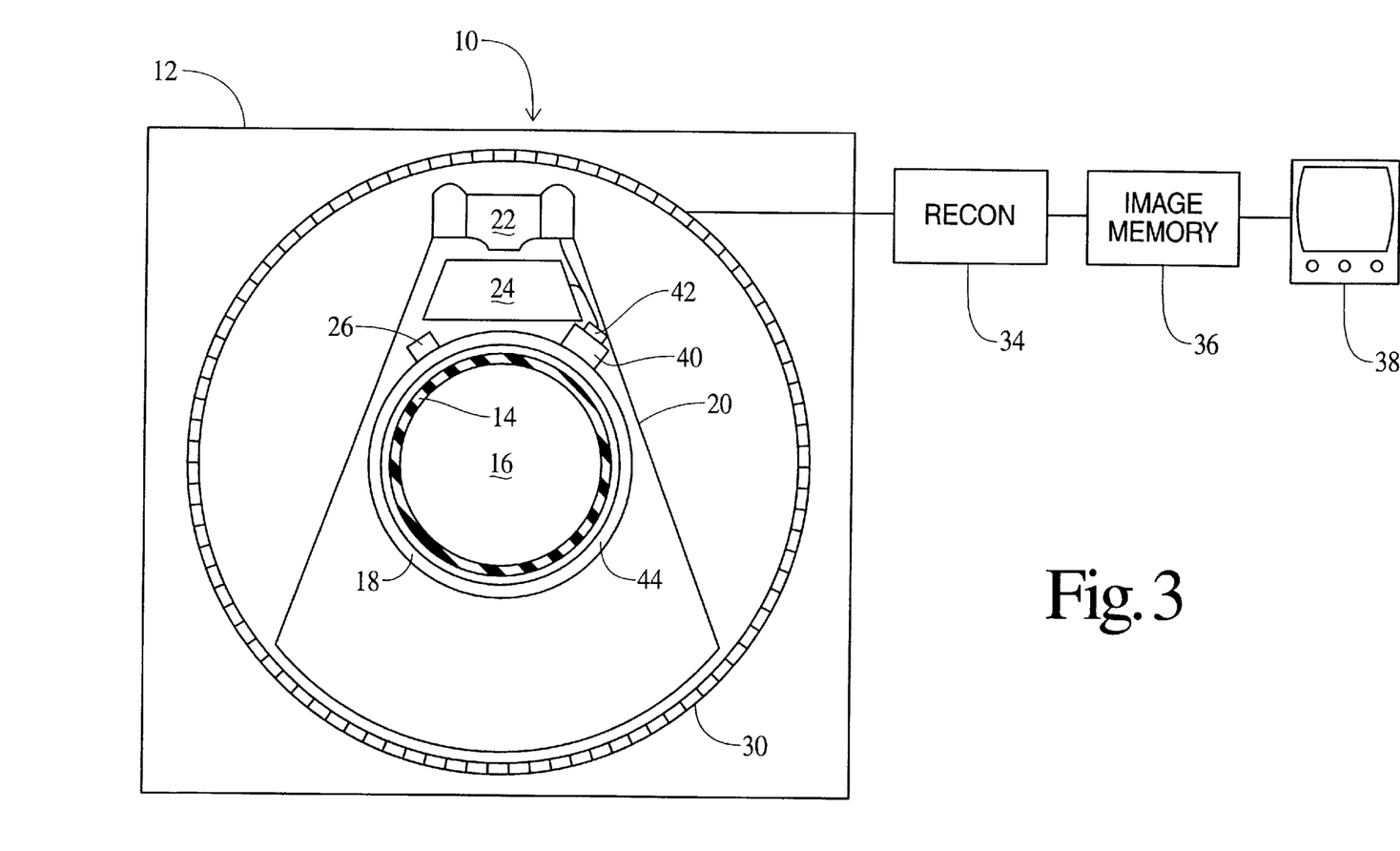
FIG. 3 is a diagrammatic illustration of an alternate embodiment of a CT scanner in accordance with an aspect of the present invention, in which radiation detectors are mounted on a stationary gantry portion and monitoring signals from a x-ray tube and shutter-collimator assembly are transmitted across the non-contact data link assembly.

The radiation detectors 30 are alternately mounted on the rotating gantry portion 20 and the stationary gantry portion 12 as shown in FIGS. 1 and 3, respectively. When mounted on the rotating gantry portion 20, the radiation detectors 30 form an arc spanning the arc of the fan shaped sheet of radiation emitted from the imaging x-ray tube 22. The radiation detectors 30 mounted on the rotating gantry portion 20 are connected with the non-contact data link assembly 32 via data handling circuitry 48. The data handling circuitry 48, in one embodiment, includes an analog to digital converter, a multiplexer, data compressor and/or other signal processing components. The non-contact data link assembly 32 transfers a signal corresponding to the output of the radiation detectors 30 from the rotating gantry portion 20 to the stationary gantry portion 12. In this case, the source of non-optical penetrating radiation 40 is mounted to the rotating gantry portion 20 and the scintillating optical fiber 44 is mounted to the stationary gantry portion 12, as shown in FIG. 2A. The scintillating optical fiber 44 is preferably mounted adjacent the slip ring assembly 18 around the subject receiving region 16 in a plane transverse to the access of rotation of the rotating gantry portion 20. As the rotating gantry portion 20 is rotated about the subject receiving region 16 relative to the stationary gantry portion 12, the output of the source of non-optical radiation 40 remains in continual alignment with the scintillating optical fiber 44.

Figure 4:
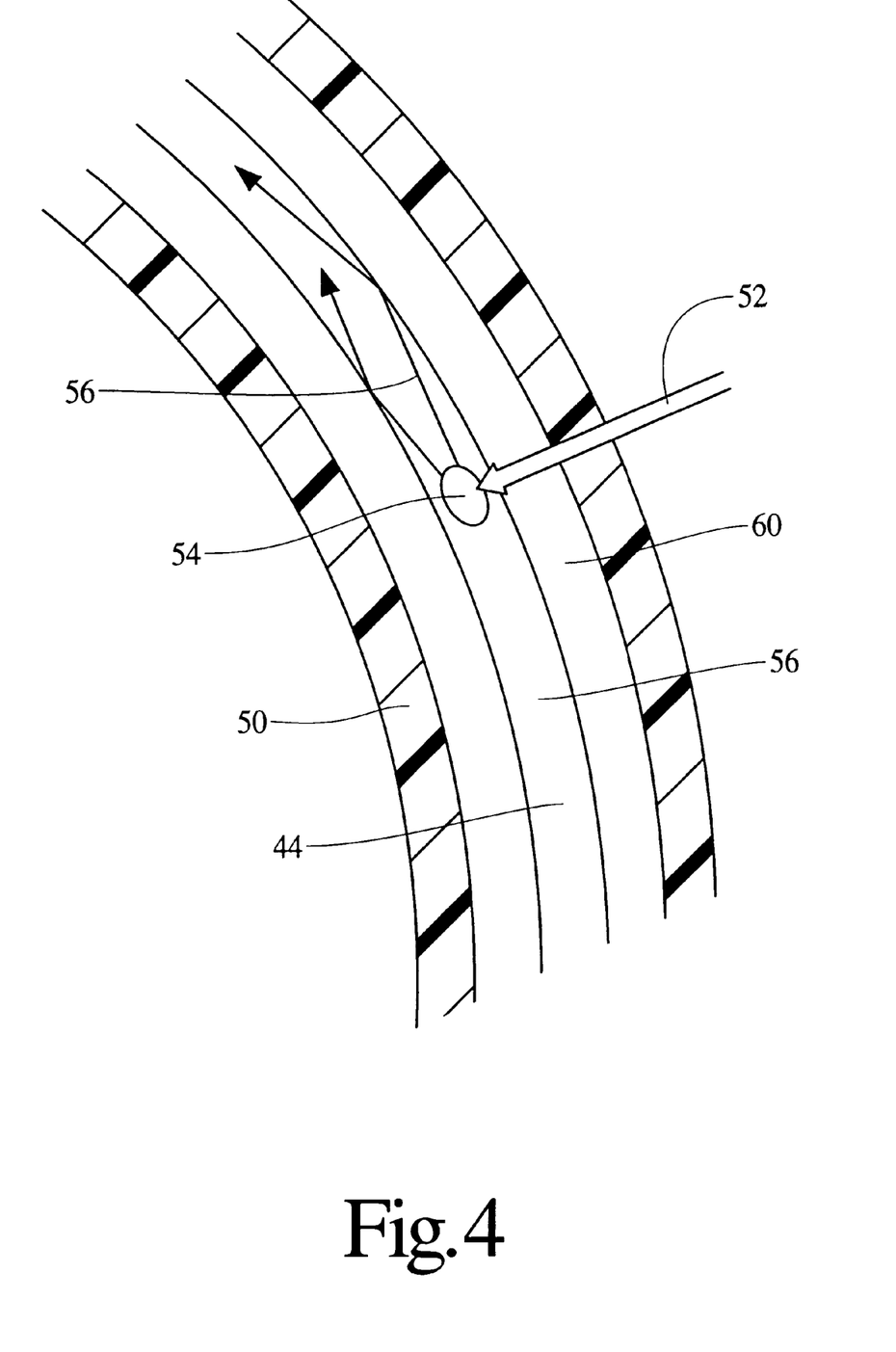
FIG. 4 is a diagrammatic illustration of a scintillating optical fiber.

As best seen in FIG. 4, the scintillating optical fiber 44, preferably, is sheathed in a tough, plastic protective covering 50 that is opaque to optical radiation in order to protect the fiber from physical damage and prevent ambient and stray light from entering the fiber. The radiation 52 from the source of non-optical radiation 40 penetrates the protective covering 50 and passes laterally into the scintillating optical fiber 44. The scintillating optical fiber 44 has a radiation sensitive dopant 54, such as a dye or particles embedded in a core 56 along the length of the fiber. The dopant is excited by x-rays or other penetrating radiation to emit optical light of a characteristic frequency. Suitable scintillator materials include rare earth scintillators, such as Gadox, $Gd_2O_2S$:Tb, $Gd_2O_2S$:Eu, and $Gd_2O_2S$:Pn. In operation, when radiation 52 incident on the fiber excites the dopant 54 within the fiber, the dopant emits light 58 which is in turn launched down the length of the fiber. Differences in the index of refraction of the core and surrounding sheathing 60. At the end of the fiber, or at pick off points along the length of the fiber, the light 58 is received by opto-electrical transducers 62 and converted into corresponding electrical signals for processing.

Figure 5A:
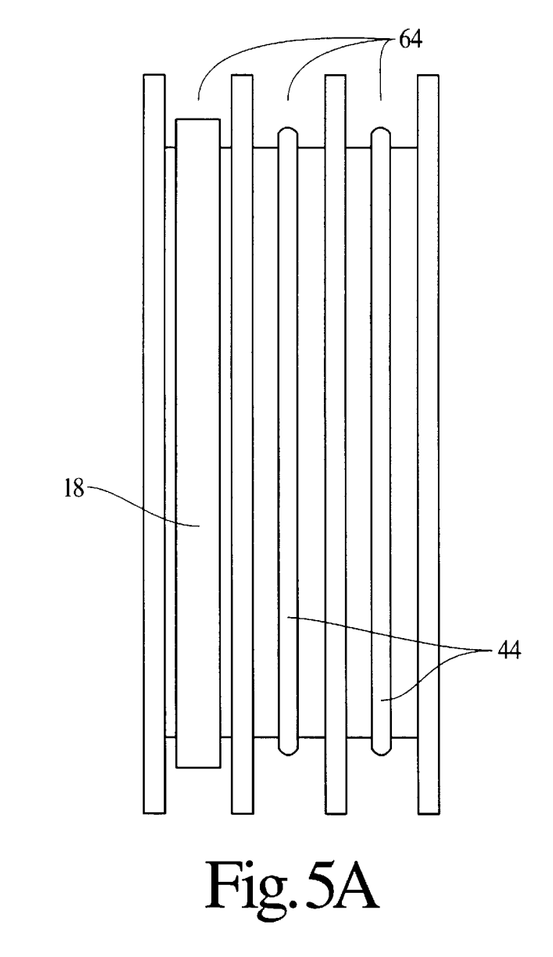
Figure 5B:
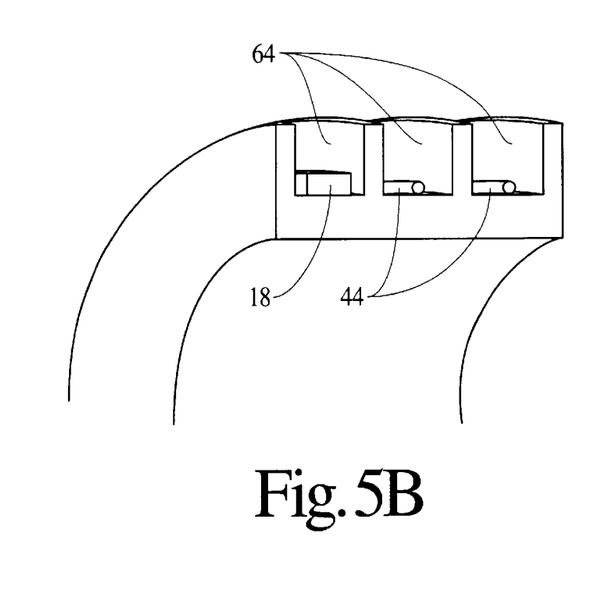
FIG. 5B shows a cut away cross sectional view; and, FIG. 6 is a diagrammatic illustration showing a light tube for use in an alternative embodiment of the present invention.

As seen in FIGS. 5A and 5B, in those instances where multiple non-contact data link assemblies 32 are employed in order to have two-way communications or for concurrent transmission of multiple signals, the individual scintillating optical fibers 44 corresponding to the signals being communicated are laid in separate channels, grooves or dividers 64 to keep the signals separated and eliminate cross talk.

Figure 6:
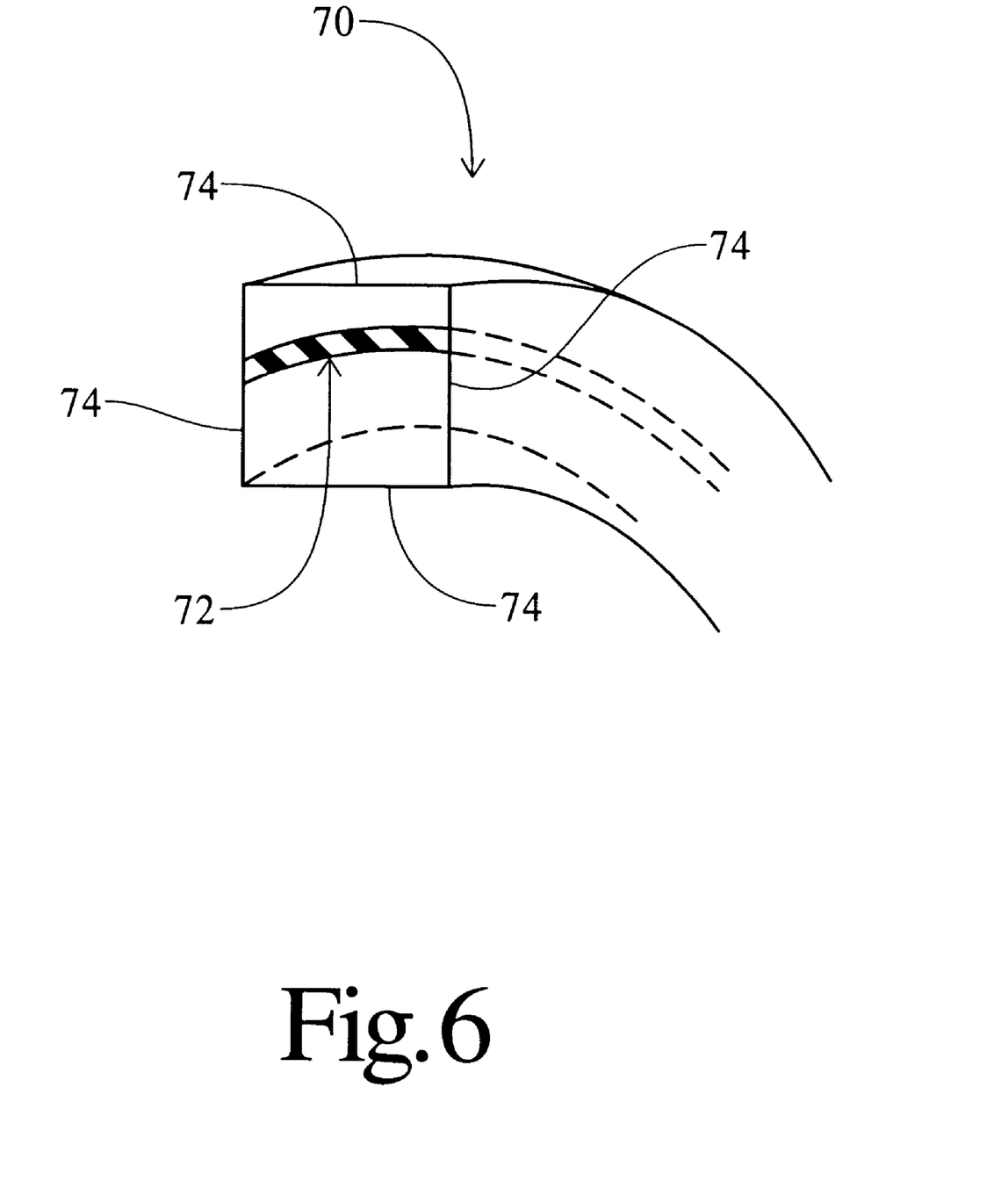

With reference to FIG. 6, in an alternate embodiment the scintillating optical fiber is replaced by a light tube 70 with a thin scintillator strip 72 applied along the inside thereof. The surfaces 74 of the hollow light tube 70 are polished and coated with a reflective material, such as gold. When the scintillator strip 72 is excited and emits light, the light is reflected from the surfaces 74 of the hollow light tube 70 down the tube where it is sampled by appropriate sensors located along its length. The tube 70 extends in a ring and is made of glass, plastics, or other suitable material. Further, while illustrated as a square cross-section tube, it may take the form of any suitable cross-section, for example round, rectangular, etc. Additionally, the outside of the tube 70 may be coated with a light opaque protective layer.

While the invention herein has been described with reference to x-ray radiation as the non-optic penetrating radiation of the non-contact data link assembly, it is appreciated that in various embodiments other forms of radiation may be employed in place thereof, such as ultraviolet radiation and others.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalence thereof.

Having disclosed the preferred embodiments, the invention is now claimed to be:

1. A radiographic scanner comprising:
   a stationary gantry portion defining a subject receiving region;
   a rotating gantry portion on which a first source of penetrating radiation is mounted, the rotating gantry portion being rotatably mounted to the stationary gantry portion for rotation about the subject receiving region;
   a non-contact data link assembly extending around the subject receiving region connected with the stationary and rotating gantry portions, the non-contact data link assembly including:
   a light tube including a scintillator mounted to extend around the subject receiving region to one of the rotating and stationary gantry portions; and,
   a second source of penetrating radiation mounted to the other gantry portion and directed such that radiation therefrom enters the lights tube, the scintillator converts incident radiation to light and transmits the light along a longitudinal axis of the lights tube.

2. The radiographic scanner according to claim 1, wherein the light tube is a scintillating optical fiber enclosed in a protective light opaque sheath.

3. The radiographic scanner according to claim 1, further including a means for modulating radiation from the second source of penetrating radiation.

4. The radiographic scanner according to claim 2, wherein the scintillating optical fiber extends along a plane transverse to an axis of rotation of the rotating gantry portion relative to the stationary gantry portion and forms a complete loop around the subject receiving region.

5. The radiographic scanner according to claim 1, wherein the non-contact data link assembly communicates control signals for controlling the first source of penetrating radiation from the stationary gantry portion to the rotating gantry portion.

6. The radiographic scanner according to claim 1, wherein the non-contact data link assembly communicates monitoring signals for monitoring operation of the first source of penetrating radiation from the rotating gantry portion to the stationary gantry portion.

7. A radiographic scanner comprising:
   a stationary gantry portion defining a subject receiving region;
   a rotating gantry portion on which a first source of penetrating radiation is mounted, the rotating gantry portion being rotatably mounted to the stationary gantry portion for rotation about the subject receiving region;
   a non-contact data link assembly extending around the subject receiving region connected with the stationary and rotating gantry portions, the non-contact data link assembly including:
   a light tube having reflective surfaces and a scintillating strip disposed therein, mounted around the subject receiving region to one of the rotating and stationary gantry portions; and,
   a second source of penetrating radiation mounted to the other gantry portion and directed such that radiation therefrom enters the light tube, the scintillating strip converts incident radiation to light and the light is reflected by the reflective surfaces down a longitudinal axis of the light tube.

8. The radiographic scanner according to claim 7, wherein the light tube is enclosed in a protective light opaque sheath.

9. In a CT scanner that includes a stationary gantry portion having a patient receiving region and a rotating gantry portion on which an imaging x-ray tube is mounted for continuous rotation around the patient receiving region about an axis of rotation, with a slip ring extending around the patient receiving region connected to one of the stationary and rotating gantry portions and a brush assembly connected to the other and in sliding contact with the slip ring for at least conveying electrical power to the imaging x-ray tube, radiation detectors mounted to one of the stationary and rotating gantry portions for detecting radiation from the imaging x-ray tube and a reconstruction processor for reconstructing an image from an output of the radiation detectors for display on a human viewable display, and a non-contact data link assembly for conveying data between the rotating and stationary gantry portions, the non-contact data link assembly comprising:

a scintillating optical fiber position adjacent the slip ring, in a plane orthogonal to the axis of rotation, and mounted to one of the rotating and stationary gantry portions, the scintillating optical fiber having an imbedded radiation sensitive dopant along its length that emits light when excited by incident radiation; and, a source of non-optical penetrating radiation mounted to the other one of the rotating and stationary gantry portions in the plane of the scintillating optical fiber, such that radiation therefrom enters the scintillating optical fiber, the scintillating optical fiber converts incident radiation therein to light and transmits the light along a longitudinal axis of the scintillating optical fiber.

10. The non-contact data link assembly as set forth in claim 9, wherein the scintillating optical fiber is covered in a protective sheathing opaque to optical radiation.

11. The non-contact data link assembly as set forth in claim 9, further including a circuit which controls the source of non-optical penetrating radiation to encode information.

12. The non-contact data link assembly as set forth in claim 9, wherein the scintillating optical fiber forms a complete loop around the patient receiving region.

13. The non-contact data link assembly as set forth in claim 9, wherein a signal for controlling the x-ray tube is transferred across the non-contact data link assembly.

14. The non-contact data link assembly as set forth in claim 9, wherein the radiation detectors are mounted to the rotating gantry portion, the output of the radiation detectors is connected to a modulator which modulates the sources of non-optical radiation mounted to the rotating gantry portion to generate a signal, the signal corresponding to the output of the radiation detectors is transferred across the non-contact data link assembly to the scintillating optical fiber mounted to the stationary gantry portion, an output of the scintillating optical fiber is connected to an opto-electrical transducer, and the opto-electrical transducer is in turn connected to the reconstruction processor.

15. A method for transferring data between stationary and rotating gantry portions of a scanner comprising:

producing a beam of non-optical radiation;

modulating the beam of non-optical radiation;

directing the modulated beam of non-optical radiation to a scintillating optical fiber;

converting the non-optical radiation incident on the scintillating optical fiber to light; and, transmitting the light along a longitudinal axis of the scintillating optical fiber.

16. The method of claim 15, wherein the step of producing includes:

producing a beam of one of (i) ultraviolet radiation with an ultraviolet source and (ii) x-ray radiation from an x-ray tube.

17. The method of claim 16, wherein the step of modulating further includes:

modulating one of a cathode to grid potential and a signal driving a cathode of the x-ray tube to vary an intensity of an electron beam within the x-ray tube.

18. The method of claim 16, wherein the step of modulating further includes:

deflecting an electron beam within the x-ray tube such that it selectively impinges two different types of anode material.

19. The method of claim 16, wherein the step of modulating further includes:

gating the beam of radiation on and off to communicate digitally.

20. The method of claim 16, wherein the step of modulating further comprises:

using a high frequency transformer to modulate an anode-cathode potential.

* * * * *